US007250097B2

(12) United States Patent
Antal et al.

(10) Patent No.: US 7,250,097 B2
(45) Date of Patent: Jul. 31, 2007

(54) DEVICE FOR SEQUENTIAL PROTEIN TRANSFER FROM A GEL

(75) Inventors: József Antal, Bethesda, MD (US); Zsuzsanna Buzás, Godollo (HU); Andreas Chrambach, Bethesda, MD (US)

(73) Assignee: The United States of America, Department of Health and Human Services, Washington, DC (US)

( * ) Notice: Subject to any disclaimer, the term of this patent is extended or adjusted under 35 U.S.C. 154(b) by 115 days.

(21) Appl. No.: 10/888,075

(22) Filed: Jul. 9, 2004

(65) Prior Publication Data

US 2005/0239092 A1    Oct. 27, 2005

Related U.S. Application Data

(60) Provisional application No. 60/566,232, filed on Apr. 26, 2004.

(51) Int. Cl.
 *G01N 27/447* (2006.01)
 *G01N 27/453* (2006.01)
(52) U.S. Cl. ............... 204/462; 204/464; 204/613; 204/614
(58) Field of Classification Search ............... 204/462, 204/464, 466, 614, 613, 616; 422/70; 435/308.1
See application file for complete search history.

(56) References Cited

U.S. PATENT DOCUMENTS 5,514,256 A * 5/1996 Douthart et al. ............ 204/464
6,001,233 A    12/1999 Levy
2002/0146839 A1* 10/2002 Guttman et al. ............ 436/177

OTHER PUBLICATIONS

Buzás et al., *An electroelution apparatus for sequential transfer of sodium dodecyl sulfate-proteins into agarose and mass spectrometric identification of Li-Na-dodectl sulfate-proteins from solubilized agarose*, 25 Electrophoresis 966 (2004).
Buzás et al., *Direct vertical electroelution of protein from a PhastSystem band for mass spectrometric identification at the level of a few picomoles*, Proteomics 2001, 1, 691-698.

(Continued)

*Primary Examiner*—Alex Noguerola
(74) *Attorney, Agent, or Firm*—Michael J. Wise; Perkins Coie LLP

(57) ABSTRACT

An apparatus and method for the sequential electroelution of biomolecules is described, the apparatus comprising a separation medium having an outlet, and a collector having at least a first receptacle and a second receptacle that can be sequentially brought into contact with the outlet of the separation medium by translating the first receptacle and the second receptacle in relation to the outlet of the separation medium, and the method comprising the steps of receiving a first substantially separated molecule in the first receptacle and translating the first receptacle and the second receptacle such that the second receptacle is brought into in contact with the outlet of the separation medium, receiving a second substantially separated molecule in the second receptacle, and repeating said steps to sequentially receive a desired number of substantially separated molecules.

51 Claims, 6 Drawing Sheets

OTHER PUBLICATIONS

Invitrogen Life Technologies, Instruction Manual, "XCell SureLock™ Mini-Cell, For leak-free electrophoresis of mini-gels," Catalog Nos. E10001, E10020, E10002, Version H, Aug. 20, 2002, *IM-9003*, pp. i-22.

Radko et al., *Electroelution without gel sectioning of proteins from sodium dodecyl sulfate-polyacrylamide gel electrophoresis: Fluorescent detection, recovery isoelectric focusing and matrix assisted laser desorption/ionization-time of flight of the electroeluate*, 23 Electrophoresis 985 (2002).

Yefimov et al., *Transfer of SDS proteins from gel electrophoretic zones into mass spectrometry, using electroelution of the band into buffer without sectioning of the gel*, J. Biochem. Biophys. Methods 42 (2000) 65-78.

* cited by examiner

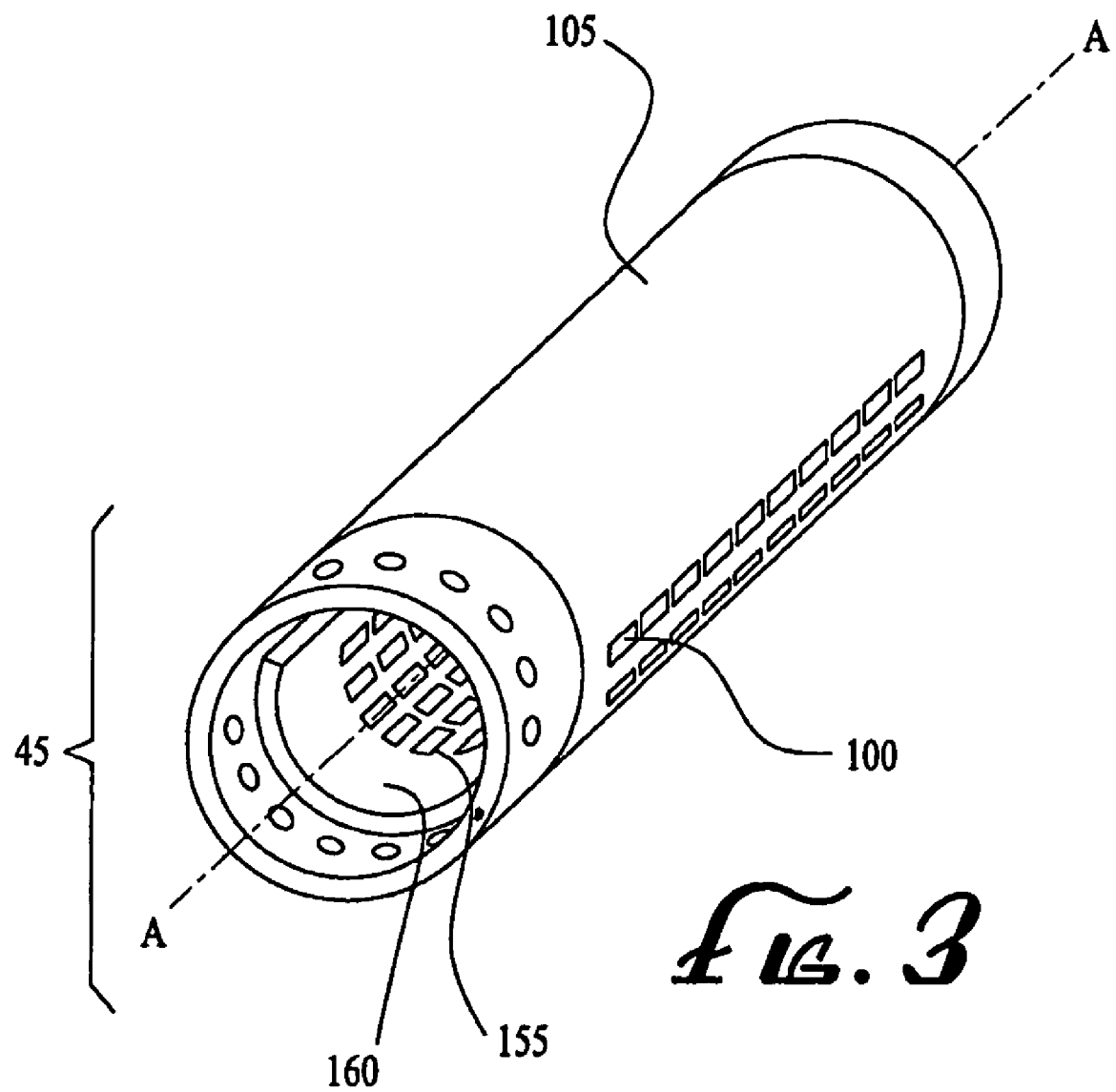

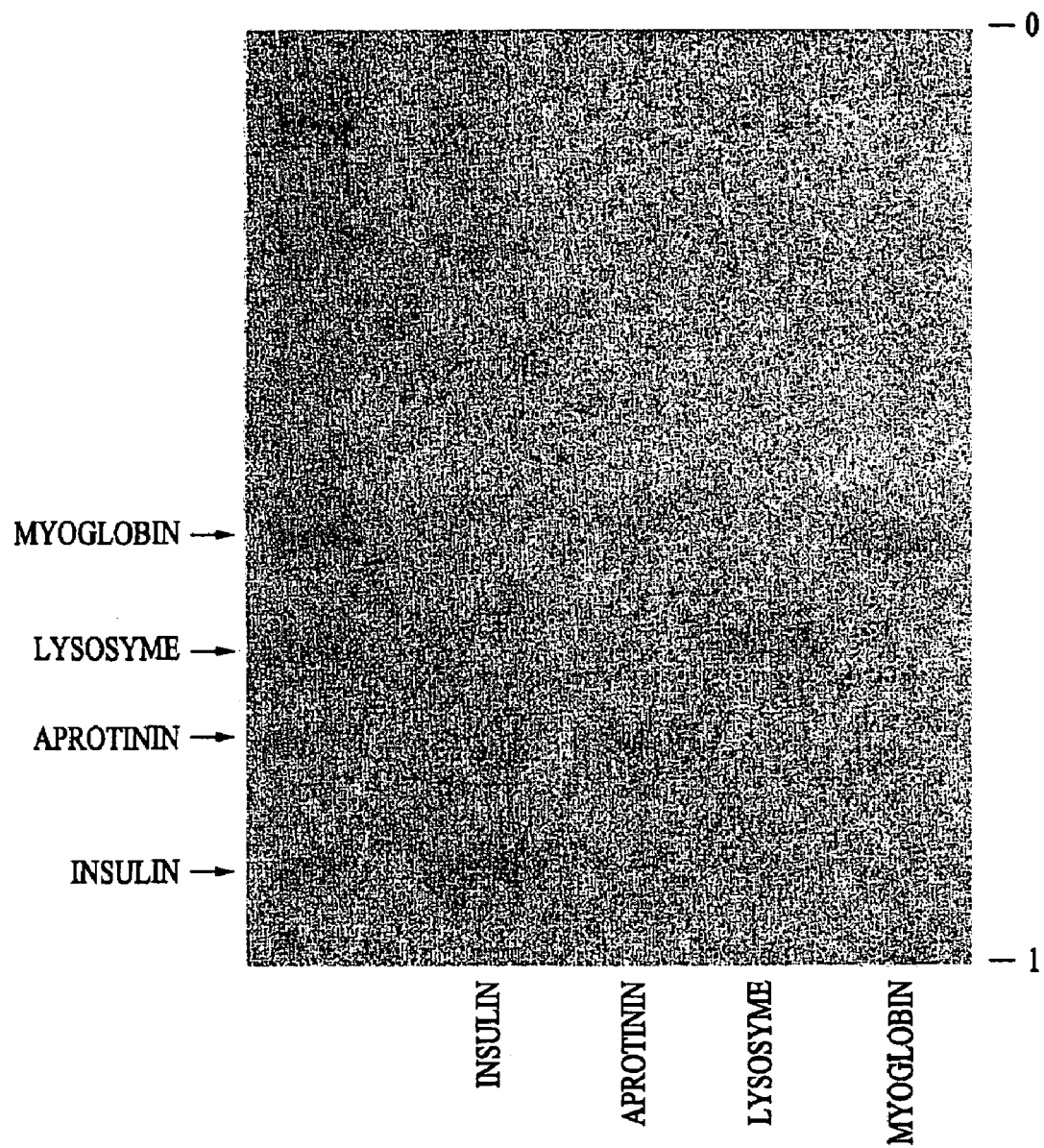

of contents in a porous matrix with pores of a desired size depending upon
DEVICE FOR SEQUENTIAL PROTEIN TRANSFER FROM A GEL

CROSS-REFERENCE TO RELATED APPLICATION

This application claims priority to U.S. Provisional Patent Application No. 60/566,232 filed Apr. 26, 2004, which is incorporated herein in its entirety by reference, including drawings.

FIELD OF THE INVENTION

The present invention relates to sequential protein transfer from a gel.

BACKGROUND OF THE INVENTION

Gel electrophoresis is commonly used to separate biomolecules such as deoxyribonucleic acids (DNA), ribonucleic acids (RNA) and proteins by molecular size. Generally, to perform electrophoresis a separation medium such as a polymeric gel is formed in a glass tube or between spaced glass or plastic sheets such that the gel forms a porous matrix with pores of a desired size depending upon the choice of gel and biomolecules to be separated. The tube or plates are placed in a container along with anode and cathode elements positioned at the top and bottom of the gel. Samples are placed in receptacles formed in the top of the gel which, during electrophoresis, result in several sample channels in the gel. Electrophoretic buffer solutions containing conductive ions are added to the container for electrical contact between the gel, samples and the cathode and anode. A voltage drop is then applied across gel causing the samples to migrate through the gel separating into bands depending upon the size of the biomolecule in relation to the porous structure of the gel. The gel can then be removed from the system and manipulated and analyzed using methods such as, e.g. blotting or gel staining.

Commercial gel electrophoresis systems are known in the art and include XCell II Mini-Cell (Novex), XCell Surelock Mini-Cell (Invitrogen), SE200 Series Min-gel System (Hoefer Pharmacia) and the Mini-PROTEAN II Electrophoresis Cell (Bio-Rad).

Because it is often desirable to analyze biomolecules separated during gel electrophoresis, many techniques exist in the art for the transfer of a biomolecule in a gel electrophoretic band (spot) to an analytical device such as mass spectrometer to identify or further analyze the biomolecule. One such method includes the step of transferring the biomolecule from an electrophoresis gel to a separate gel plug (electroelution) which can then be further manipulated for analysis by, for example, destaining and extraction. The prevalent approach to such identification includes the excision of the gel band followed by the in situ proteolysis of the spot and extraction of the biomolecules by either diffusion or electrophoresis. Attempts have been made in the art to perform the electroelution on the electropherogram directly, i.e. without slicing the gel. Attempts have also been made to include intermediate steps such as testing for homogeneity after electroelution, identification of the protein by its intact mass independently of proteolysis and identification of a protein on the basis of its peptide map. Other methods in the art include elution or electroelution of biomolecules into a collection chamber, direct positioning of gel pieces containing a band onto the receptacle of a mass spectrometer, and blotting of the gel membrane followed by direct mass spectrometric analysis of the blot.

The aforementioned techniques require extensive time and effort because the separated biomolecules cannot be sequentially electroeluted for subsequent manipulation or analysis. Because of the foregoing reasons there is a desire in the art for a method and apparatus for the sequential electroelution of multiple biomolecule bands contained in a separation gel.

SUMMARY OF THE INVENTION

It is an object of the present invention to provide a method for sequential electroelution of a biomolecule band.

It is another object of the present invention to provide an apparatus for the sequential electroelution of a biomolecule band.

These and other aspects of the present invention which may become obvious to those skilled in the art through the following description of the invention are achieved by a method and apparatus for the sequential electroelution of a biomolecule band.

In one embodiment of the invention, an apparatus according to the present invention is disclosed comprising a separation medium having an outlet, and a collector having at least a first receptacle and a second receptacle that can be sequentially brought into contact with the outlet of the separation medium by translating the first receptacle and the second receptacle in relation to the outlet of the separation medium.

In a second embodiment of the invention, a method according to the present invention is disclosed comprising the steps of receiving a first substantially separated molecule in a first receptacle of an apparatus comprising a separation medium having an outlet and a collector having at least the first receptacle and a second receptacle wherein the first receptacle and the second receptacle can be sequentially brought into contact with the outlet of the separation medium by translating the first receptacle and the second receptacle in relation to the outlet of the separation medium, translating the first receptacle and the second receptacle such that the second receptacle is brought into in contact with the outlet of the separation medium, receiving a second substantially separated molecule in the second receptacle, and repeating said steps to sequentially receive a desired number of substantially separated molecules.

BRIEF DESCRIPTION OF THE DRAWINGS

FIG. 3 shows the collection drum of the apparatus of FIG. 1.

FIG. 4 shows a sample of proteins that has been separated.

DETAILED DESCRIPTION OF PREFERRED EMBODIMENTS

In order to fully understand the manner in which the above-recited details and other advantages and objects according to the invention are obtained, a more detailed description of the invention will be rendered by reference to specific embodiments thereof.

As used herein, a "biomolecule" is defined as an organic molecule. A biomolecule is typically found in living organisms, and includes but is not limited to peptides or proteins, which may be labeled by various means, double and single stranded nucleic acids, DNA or RNA.

Figure 1:
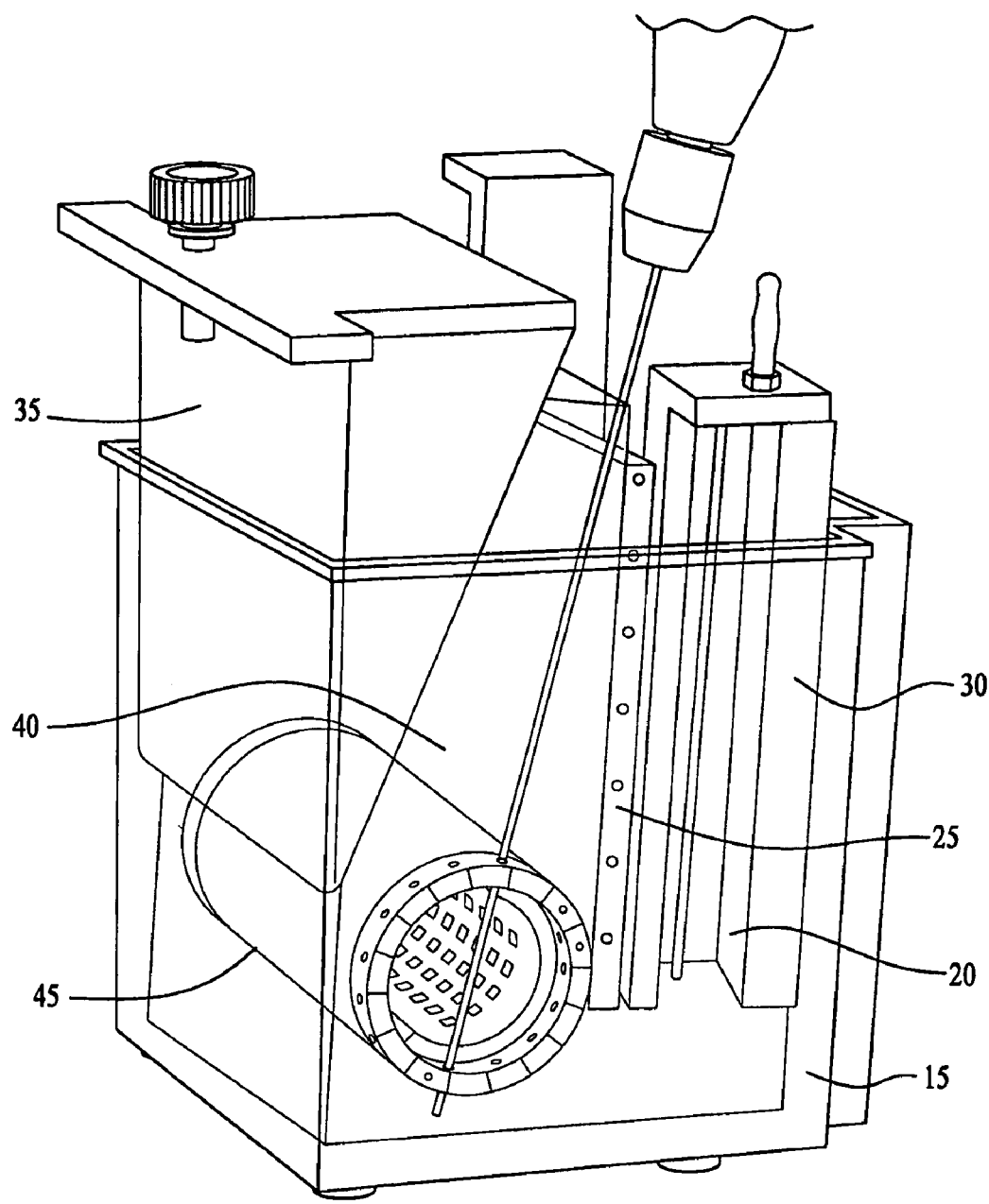
FIG. 1 an apparatus according to the present invention.

Referring to FIG. 1, an apparatus for the sequential transfer of separated biomolecule bands according to the present invention is described comprising a tank 15, a buffer core 20, a gel cassette 25, a buffer dam 30, rear wedge 35, a gel tension wedge and drum holder 40, and a collector whereby the collector comprises a collection drum 45.

Figure 2A:
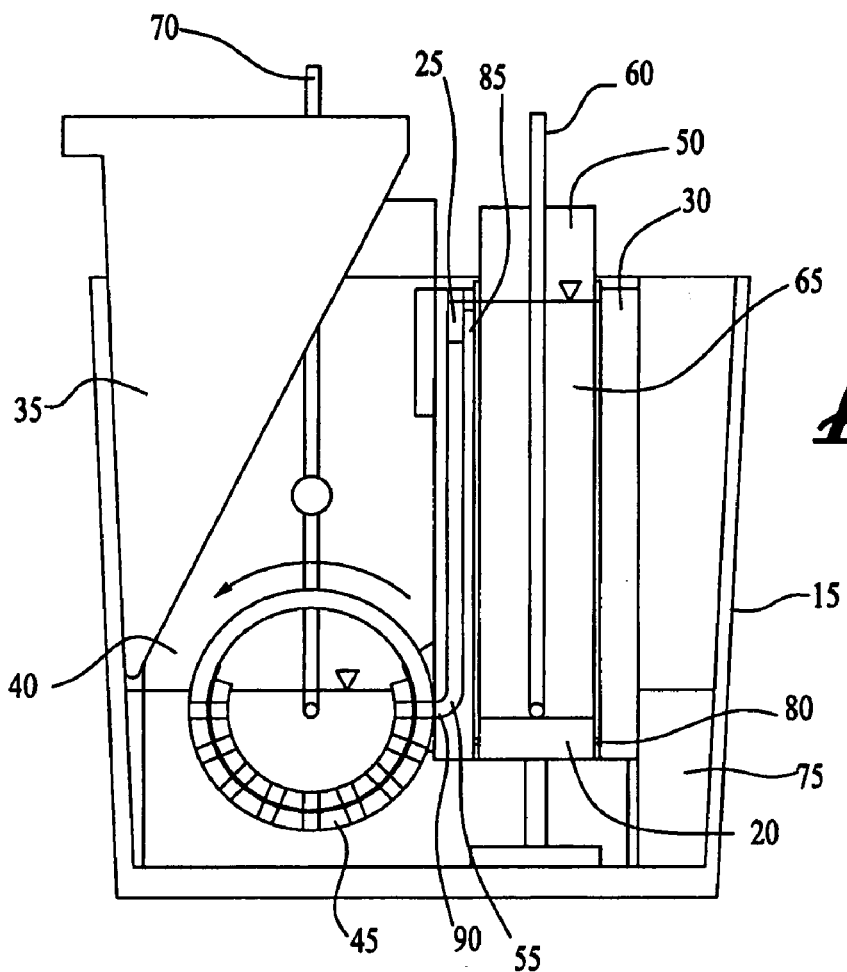
FIG. 2A a cross-sectional view of the apparatus of FIG. 1.

Referring to FIG. 2A, a cross-sectional view of the apparatus according to the present invention is shown whereby the tank 15 is configured with a bottom and four sides and is open at the top to receive the remaining parts of the apparatus. The gel tension wedge and drum holder 40 in combination with the rear wedge 35 is configured such that when placed into the tank 15 it holds in place the collection drum 45 such that the collection drum 45 may still rotate when desired. The gel tension wedge and drum holder 40 and the rear wedge further hold in place the gel cassette 25, buffer core 20 and the buffer dam 30 such that a chamber 50 is formed in the apparatus.

The gel cassette 25 is configured to contain a separation gel 55 in communication with the buffer chamber 50 at the top 85 and in communication with the collection drum 45 at the bottom 90. When assembled, the buffer chamber 50 is configured to receive a cathode 60 and catholyte 65 and a portion of the tank 15 is configured to receive an anode 70 and anolyte 75 such that the catholyte 65 and anolyte 75 are not in direct fluid communication and are separated by the buffer core 20, gel cassette 25, buffer dam 30 and seals 80 as needed. In the alternative, it is contemplated that the apparatus could be configured such that the catholyte 65 and anolyte 75 are in fluid communication or are the same electrolyte if desired.

Figure 2B:
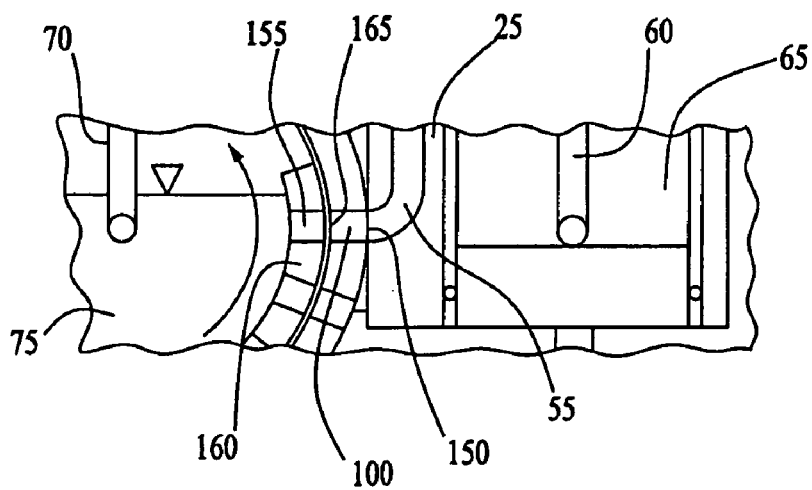
FIG. 2B shows a portion of the cross-section of FIG. 2 which has been enlarged.

Referring to FIG. 3, the collection drum 45 of the apparatus is shown comprising receptacles whereby the receptacles comprise outer slots 100 for containing a slot gel along its lateral surface 105 having the preferred dimension of 2 mm by 5 mm, where by each individual outer slot 100 is separated from adjoining outer slots 100 by 2 mm. Referring to FIGS. 2B and 3, the collection drum 45 is configured such that it can mechanically rotate along its horizontal axis A—A causing the movement of the outer slots 100 in relation to the separation gel 55 whereby each outer slot 100 is brought into contact sequentially with the separation gel 55 such that a contact surface 150 is formed between the slot gel and the separation gel for each successive outer slot 100 as the drum is rotated. Preferably the slot gel is an agarose gel or similar but can be any material acceptable to receive a biomolecule for further processing and analysis. The collection drum 45 further comprises membrane holder slots 155 where each membrane holder slot 155 corresponds to an outer slot 100 and is configure to receive a membrane, the membrane holder slots 155 are in communication with membrane holders 160. The collection drum 45 is configured such that it can be manually rotated when desired. In the alternative, it is contemplated that the rotation of the collection drum 45 may be effected by automated mechanical means known to one skilled in the art such as electronically controlling the rotation of the collection drum 45 by coupling the collection drum 45 to a motor and a microprocessor such that the microprocessor can be programmed to rotate the drum in the desired manner.

Referring to FIG. 2B, the gel cassette 25 is configured to contain a separation gel 55. The separation gel 55 may be any gel known in the art, such as a polyacrylamide gel, suitable for the intended separation and is selected based on the pore size of the formed gel in relation to the biomolecules to be separated. The gel cassette 25 is configured such that a contact surface 150 is formed between the slot gel in an outer slot 100 in the collection drum 45 and the separation gel 55 in the gel cassette 25.

A method according to the present invention is now described. Referring to the apparatus of FIGS. 1–3, the sequential transfer of separated biomolecule bands according to the present invention is described where separated biomolecule bands are electrophoresed into a slot gel plug, preferably low melting agarose plugs, distributed along the surface 105 of the collection drum 45 by rotating the collection drum 45 to receive each biomolecule band individually. The slot gel plugs are then dissolved enzymatically for transfer to a detection device such as a mass spectrometer.

Protein mixtures may be separated by electrophoresis such as sodium dodecyl sulfate (SDS) polyacrylamide gel electrophoresis (PAGE) with an 2-(N-Morpholino)ethanesulfonic acid (MES)-SDS running buffer. It is contemplated that other types of electrophoresis may be employed with the present method depending on the specific molecules to be isolated and analyzed, which may be selected by one skilled in the art. It is also contemplated that other gels and running buffers may be selected by one skilled in the art depending on the specific application. Finally, it is contemplated that the present method could be adapted to two-dimensional electrophoresis.

During electrophoretic separation of biomolecules, as a migrating biomolecule band enters into an elution channel of apparatus, it is electrophoresed into one of the outer slots 100 of the collection drum 45 which contains a plug of a slot gel such as 1% Sea Plaque GTG low buffer melting agarose (Bio Whittaker, Walkersville, Md.) prepared in the running buffer. The slot gel may be selected by one skilled in the art depending on the specific application. The preferred slot gel is low melting agarose which melts at 65–70° C. and stays molten a 45° C. which allows for ease in further processing of the sample after electroelution.

The anodic side 165 of the plugs is covered with a membrane 155 selected by one of skill in the art such that the slot gel and eluted protein band is retained in the slot gel plug in the outer slot 100. Electrical contact is accomplished by filling the contact zone between the elution channel of the separation gel 55 and the slot gel with running buffer just prior to electrophoresis, such as 1% Sea Plaque GTG agarose prepared in MES-SDS running buffer.

The effective electroelution of a protein from a gel band to a slot gel plug requires sufficient contact 150 between the separation gel 55 and the slot gel as shown in FIG. 3A. By rotation of the collection drum 45, the outer slots 100 are positioned on the collection drum 45 in apposition to the, for example, ten sample lanes of the gel cassette 25. More or less sample lanes could be formed in the gel of the gel cassette 25 depending on the desired size and configuration of the gel cassette 25. As biomolecule bands appear sequentially in the slot gel plugs, the voltage drop across the anode and cathode is discontinued, and the collection drum 45 rotated to make contact between the next row of outer slots 100 to accept the next set of biomolecule bands as they migrate sequentially through each of the channels of the gel cassette 25 into their corresponding outer slot 100. One may detect when the biomolecule bands appear in the slot gel plugs by visual inspection or through other detection means known in the art. The aforementioned steps are then repeated until the outer slots 100 containing slot gel plugs sequentially receive each of the separated biomolecules in substantially homogeneous form.

The individual slot gel plugs are lifted from the slots by spatula which can then be further processed and/or analyzed. For example, the slot gel plug containing the biomolecule band of interest can be dissolved at an elevated temperature, subsequently cooled and then digested by a gel-digesting preparation or similar for loading directly onto a detection device such as a mass spectrometer for further analysis. The current method has been applied to colored proteins but it is contemplated that it could be adapted for methods employing fluorescent labeling of the biomolecule and laser optical detection as described in Radko et al., *Electroelution without gel sectioning of proteins from sodium dodecyl sulfate-polyacrylamide gel electrophoresis: Fluorescent detection, recovery isoelectric focusing and matrix assisted laser desorption/ionization-time of flight of the electroeluate*, 23 Electrophoresis 985 (2002), incorporated herein in its entirety by reference. The method may also be adapted for use with capillary electrophoresis such as described in Pohl, F. M. & Beck, S., *Direct transfer electrophoresis used for DNA sequencing*, 155 Methods in Enzymology 250 (1997), incorporated herein in its entirety by reference.

EXAMPLE I

An example according to the present invention is now described.

Color standard SDS-protein mixtures (MultiMark Multi Colored Standard, Invitrogen, Carlsbad, Calif.) were separated by sodium dodecyl sulfate (SDS) polyacrylamide gel electrophoresis (PAGE) on a commercial NuPAGE 12% Bis-Tris gel (Invitrogen) in MES-SDS running buffer. As the migrating SDS-protein band enters into the elution channel of the apparatus, it is electrophoresed into the receptacle slots 100 of collection drum 45, containing plugs of 1% Sea Plaque GTG low buffer melting agarose (Bio Whittaker, Walkersville, Md.) prepared in the running buffer.

An example of a separated mixture is shown in FIG. 4 where four proteins from a MultiMark Colored SDS-protein mixture were first electroeluted into agarose plugs by the present method and then subjected to re-electrophoresis.

The agarose used is atypical of most standard agarose which requires temperatures of 85–95° C. to melt. Instead, the low melting agarose employed in the present example melts at approximately 65–70° C. and stays molten at approximately 45° C.

The anodic side 165 of the plugs is covered with a membrane 155 (3,500 MWCO, Pierce, Rockford Ill.). Electrical contact is secured by filling the contact zone between the elution channel of the polyacrylamide gel and the agarose plug with 1% SeaPlaque GTG agarose prepared in MES-SDS running buffer just prior to electrophoresis.

The effective electroelution of a protein from a gel band to an agarose filled slot depends on the contact 150 between the polyacrylamide gel and the agarose plug as shown in FIG. 3A. By rotation of the collection drum 45, the outer slots 100 are positioned on the collection drum 45 in apposition to the ten sample lanes of the gel cassette 25. As colored bands appear sequentially in the agarose plugs, the voltage drop across the anode and cathode is discontinued, and the collection drum 45 is rotated to make contact between the plugs and the protein bands migrating sequentially through gel cassette 25. The steps are then repeated until each of the separated bands is sequentially collected in homogeneous form in the agarose plugs.

The agarose plugs are then lifted from the slots by spatula for further analysis. The agarose plug containing band of interest in MES-SDS buffer is dissolved at 70° C., cooled to 45° C., digested by GELase agarose gel-digesting preparation with addition of GELase buffer (Epicentre, Madison Wis.) at 45° C. for 1 hour, and can be loaded directly onto a matrix-assisted laser desorption ionization (MALDI) mass spectrometer. The GELase preparation contains a unique beta-agarose digesting enzyme, which digests long-chain polysaccharides in molten agarose, releasing small, soluble oligosaccharides and giving a clear liquid that does not solidify on cooling to room temperature.

Mass spectrometric analysis as described above has been shown to be effective with good sensitivity without any purification from SDS of the agarose solution prior to the transfer to the mass spectrometer. It is contemplated that use of the present method is potentially capable of transferring less than 1 picomole of SDS protein to a MALDI mass spectrometer with acceptable sensitivity even when the agarose solution is transferred directly to the MALDI mass spectrometer.

Figure 5:
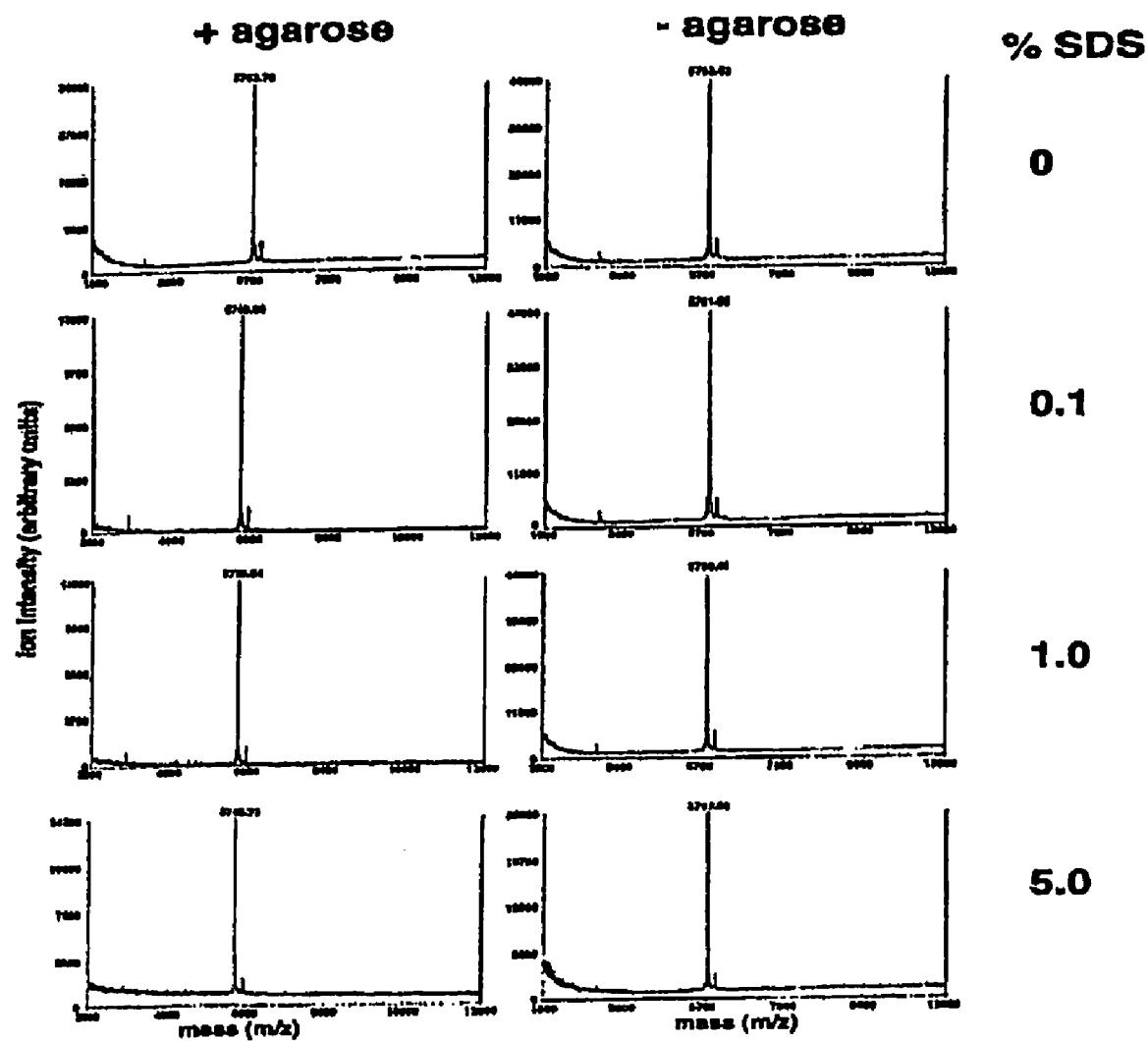
FIG. 5 shows MALDI mass spectrometry patterns of 1 picomole samples of Li—Na-DS insulin with and without agarose.
Figure 6:
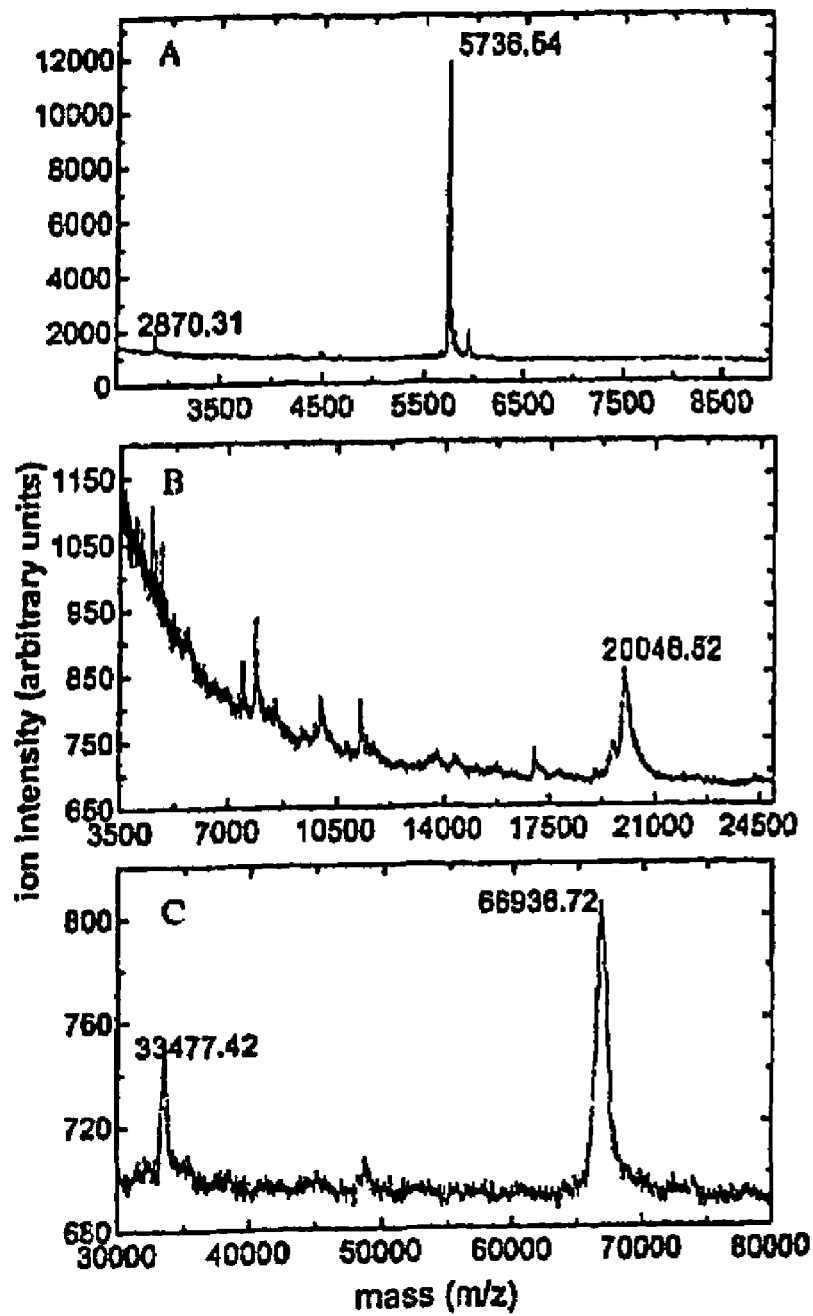
FIG. 6 shows the dependence of signal in MALDI mass spectrometry of 1 picomole loads of Li—Na-DS-proteins as a function of their molecular weights.

Referring to FIG. 5, the intensity of the signal of the agarose solubilized Li-NA-DS-insulin in MALDI mass spectrometry is shown to be independent of SDS concentration in the range of 0% to 5%. Referring to FIG. 6, the detection sensitivity of proteins by MALDI mass spectrometry is shown to decrease with molecular mass from 6 for insulin to 20 for soybean trypsin inhibitor (STI) to 67 for bovine serum albumin (BSA) kDa. For the analysis of the lithium and natrium salts of dodecyl sulfate (Li—Na-SDS)-proteins of insulin, STI and BSA in 1% SeaPlaque agarose solubilized in NuPAGE MOPS-SDS buffer (50 mM MOPS, Tris-base, 1 mM EDTA, 0.1% SDS) shown in FIGS. 5 and 6, the protein samples were prepared in 2% Li-DS (not SDS) by heating the protein samples at 70° C. for 10 minutes in NuPAGE Li-DS sample buffer (141 mM Tris-base, 106 mM Tris-HCl, 2% Li-DS, 10% glycerol, 0.51 mM EDTA). The temperature condition (70° C.) minimized protein cleavage during sample preparation. SDS was added to the solubilized agarose, mimicking that constituting the electroeluate solution of Li-Na—DS-proteins in the concentrations specified. One picomole of Li—Na-DS-proteins was applied without any desalting or purification of the proteins (i.e., removal of agarose, SDS, Li-DS, components of GELase preparation, etc.) prior to MALDI analysis. The aforementioned results are described in Buzas et al., *An electroelution apparatus for sequential transfer of sodium dodecyl sulfate-proteins into agarose and mass spectrometric identification of Li—Na-dodecyl sulfate-proteins from solubilized agarose*, 25 Electrophoresis 966 (2004), incorporated herein in its entirety by reference.

A further embodiment of the invention is a kit for conducting electrophoretic separation of biomolecules comprising a separation medium having an outlet and an inlet, a collector comprising at least a first receptacle and a second receptacle that can be brought into contact with the outlet of the separation medium by translating the first receptacle and the second receptacle in relation to the outlet of the separation medium, an anode and a cathode as describer herein. The kit may further comprise additional components useful in electrophoretic separation of biomolecules such as electrolyte or a separation gel that may contained in an interchangeable precast separation gel cassette such that the kit can be used for multiple separations by interchanging the precast gel cassette.

While the invention is described in terms of specific embodiments, other embodiments could readily be adapted by one skilled in the art. Accordingly, the scope of the present invention is limited only by the following claims.

The invention claimed is:

1. An apparatus for sequentially receiving molecules from a separation medium comprising:
   a separation medium comprising an outlet; and
   a collector comprising at least a first receptacle and a second receptacle that can be sequentially brought into contact with the outlet of the separation medium by translating the first receptacle and the second receptacle in relation to the outlet of the separation medium, wherein at least the first receptacle of the collector comprises a gel to receive a molecule.

2. The apparatus of claim 1 wherein the first receptacle comprises a slot and the second receptacle comprises a slot.

3. The apparatus of claim 2 wherein the separation medium comprises a separation gel suitable for use in electrophoresis.

4. The apparatus of claim 3 wherein the separation gel comprises a polyacrylamide gel.

5. The apparatus of claim 3 wherein the collector comprises a collection drum.

6. The apparatus of claim 5 wherein the collection drum is rotated by mechanical rotation.

7. The apparatus of claim 5 wherein the collection drum is rotated by automated mechanical rotation.

8. The apparatus of claim 5 wherein at least a first slot and second slot of the collection drum comprises a slot gel to receive the molecule.

9. The apparatus of claim 8 further comprising a membrane in communication with the slot gel opposite the separation gel for retaining the slot gel and the molecule.

10. The apparatus of claim 9 wherein the slot gel comprises agarose.

11. The apparatus of claim 9 further comprising an analysis device.

12. The apparatus of claim 1 wherein the gel of the first receptacle and second receptacle comprises agarose.

13. An apparatus for sequentially electroeluting biomolecules from an electrophoresis separation medium comprising:
    an electrophoresis separation medium comprising an outlet; and
    a collection drum comprising at least a first slot and a second slot that can be sequentially brought into contact with the outlet of the separation medium by translating the first slot and the second slot in relation to the outlet of the separation medium.

14. The apparatus of claim 13 wherein the collection drum is rotated by mechanical rotation.

15. The apparatus of claim 13 wherein the collection drum is rotated by automated mechanical rotation.

16. A method for sequentially receiving molecules from a separation medium for use in a separation method comprising the steps of:
    receiving a first substantially separated molecule in a first receptacle of an apparatus comprising a separation medium having an outlet and a collector having at least the first receptacle and a second receptacle wherein at least the first receptacle of the collector comprises a gel to receive a molecule and wherein the first receptacle and the second receptacle can be sequentially brought into contact with the outlet of the separation medium by translating the first receptacle and the second receptacle in relation to the outlet of the separation medium;
    translating the first receptacle and the second receptacle such that the second receptacle is brought into contact with the outlet of the separation medium;
    receiving a second substantially separated molecule in the second receptacle; and
    repeating said steps to sequentially receive a desired number of substantially separated molecules.

17. The method of claim 16 wherein the first receptacle comprises a slot and the second receptacle comprises a slot.

18. The method of claim 17 wherein the molecules comprise biomolecules.

19. The method of claim 18 wherein the biomolecules are selected from the group consisting of DNA, RNA and proteins.

20. The method of claim 19 wherein the separation method comprises gel electrophoresis.

21. The method of claim 20 wherein the separation medium comprises a separation gel suitable for use in electrophoresis.

22. The method of claim 21 wherein the separation gel comprises a polyacrylamide gel.

23. The method of claim 21 wherein the collector comprises a collection drum.

24. The method of claim 23 wherein the collection drum is rotated by mechanical rotation.

25. The method of claim 23 wherein the collection drum is rotated by automated mechanical rotation.

26. The method of claim 23 wherein at least a first slot and second slot of the collection drum comprise a slot gel to receive the molecule.

27. The method of claim 26 further comprising a membrane in communication with the slot gel opposite the separation gel for retaining the slot gel and the molecule.

28. The method of claim 27 wherein the slot gel comprises agarose.

29. The method of claim 26 further comprising the step of analyzing at least one of the substantially separated molecules.

30. The method of claim 26 wherein the analysis of the at least one biomolecule is by mass spectrometry.

31. The method of claim 16 wherein the gel of the first receptacle and second receptacle comprises agarose.

32. A method for sequentially electroeluting biomolecules from an electrophoretic separation medium comprising the steps of:
    receiving a first substantially separated biomolecule in a first slot of an apparatus comprising a separation gel having an outlet and a collection drum having at least the first slot and a second slot wherein the first slot and the second slot can be sequentially brought into contact with the outlet of the separation gel by translating the first slot and the second slot in relation to the outlet of the separation gel and wherein the first slot and the second slot comprise a slot gel;
    translating the first slot and the second slot such that the second slot is brought into in contact with the outlet of the separation gel;
    receiving a second substantially separated biomolecule in the second slot;
    repeating said steps to sequentially receive a desired number of substantially separated biomolecules; and
    analyzing at least one of the substantially separated biomolecules.

33. The method of claim 32 wherein the analysis of the at least one substantially separated molecule is by mass spectrometry.

34. The method of claim 33 wherein the separation gel comprises a polyacrylamide gel.

35. The method of claim 34 wherein the slot gel comprises agarose.

36. The method of claim 32 wherein the collection drum is rotated by mechanical rotation.

37. The method of claim 32 wherein the collection drum is rotated by automated mechanical rotation.

38. A kit for conducting electrophoretic separation of biomolecules comprising:
   a separation medium having an outlet and an inlet;
   a collector comprising at least a first receptacle and a second receptacle that can be sequentially brought into contact with the outlet of the separation medium by translating the first receptacle and the second receptacle in relation to the outlet of the separation medium, wherein at least the first receptacle of the collector comprises a gel to receive a molecule;
   an anode; and
   a cathode.

39. The kit of claim 38 wherein the kit further comprises an electrolyte.

40. The kit of claim 38 wherein the separation medium further comprises as separation gel.

41. The kit of claim 40 further comprising a gel cassette configured to contain the separation gel.

42. The kit of claim 41 wherein the separation gel comprises a polyacrylamide gel.

43. The kit of claim 42 wherein the collector comprises a collection drum.

44. The kit of claim 43 wherein the first receptacle comprises a first slot and the second receptacle comprises a second slot.

45. The kit of claim 44 wherein the at least first slot and second slot of the collection drum comprises a slot gel to receive the molecule.

46. The kit of claim 45 wherein the collector further comprises a membrane in communication with the slot gel opposite the separation gel for retaining the slot gel and a substantially separated biomolecule.

47. The kit of claim 46 wherein the slot gel comprises agarose.

48. The kit of claim 47 wherein the collection drum is rotated by mechanical rotation.

49. The kit of claim 48 wherein the collection drum is rotated by automated mechanical rotation.

50. The kit of claim 40 further comprising a pre cast interchangeable gel cassette configured to contain the separation gel.

51. The kit of claim 38 wherein the gel of the first receptacle and second receptacle comprises agarose.

* * * * *